United States Patent [19]

Garrou

[11] 4,374,999

[45] Feb. 22, 1983

[54] INTERNAL HYDROFORMYLATION OF ACROLEIN ACETALS

[75] Inventor: Philip E. Garrou, Holliston, Mass.

[73] Assignee: The Dow Chemical Company, Midland, Mich.

[21] Appl. No.: 222,184

[22] Filed: Jan. 2, 1981

[51] Int. Cl.³ .................. C07D 317/10; C07D 319/04; C07C 43/00

[52] U.S. Cl. .................................... 549/453; 568/451; 568/455; 568/599; 568/600; 568/882; 568/909; 549/374

[58] Field of Search .......................... 260/340.7, 340.9; 568/600, 451, 455, 599, 882, 909; 549/374, 453, 375, 454

[56] References Cited

U.S. PATENT DOCUMENTS

| | | | |
|---|---|---|---|
| 3,929,915 | 12/1975 | Cumbo et al. | 260/340.7 |
| 3,947,503 | 3/1976 | Kummer | 260/340.7 |
| 4,017,550 | 4/1977 | Kummer | 260/340.7 |
| 4,052,401 | 10/1977 | Hughes | 549/375 |
| 4,072,720 | 2/1978 | Haag et al. | 568/882 X |
| 4,079,064 | 3/1978 | Taylor | 549/374 |
| 4,105,677 | 8/1978 | Taylor | 549/375 |
| 4,144,191 | 3/1979 | Hartwell et al. | 568/819 |
| 4,197,414 | 4/1980 | Hartwell et al. | 568/831 |
| 4,209,467 | 6/1980 | Kojima et al. | 549/375 |
| 4,209,643 | 6/1980 | Shin | 568/600 |
| 4,213,921 | 7/1980 | Mitchell et al. | 568/455 |
| 4,301,090 | 11/1981 | Pesa et al. | 568/600 |

FOREIGN PATENT DOCUMENTS 53-68709 6/1978 Japan .

*Primary Examiner*—Ethel G. Love
*Attorney, Agent, or Firm*—Charles J. Enright

[57] ABSTRACT

Acrolein acetals are selectively hydroformylated on the unsaturated carbon atom adjacent to the carbon bearing two ether groups in the presence of a supported rhodium-cobalt bimetallic cluster. The resulting internally hydroformylated product is useful as a precursor of methacrylic acid.

6 Claims, No Drawings

INTERNAL HYDROFORMYLATION OF ACROLEIN ACETALS

BACKGROUND OF THE INVENTION

This invention relates to a process for selectively hydroformylating an acrolein acetal on an unsaturated carbon atom other than the terminal carbon atom. More particularly, this is a one-step process for effecting such hydroformylation using as a catalyst an amine-resin supported rhodium-cobalt carbonyl bimetallic cluster.

U.S. Pat. Nos. 4,144,191 and 4,197,414 disclose the use of rhodium-cobalt carbonyl bimetallic clusters supported by amine resins as catalysts for the hydroformylation of olefins. These patents teach that any olefin that can be converted to an aldehyde by known oxo processes can be converted to alcohols by the process described therein. The distribution of isomers in the hydroformylated product is not disclosed, but the distribution of alcohol isomers would be expected to be similar to the aldehyde distribution obtained with the prior art oxo process.

U.S. Pat. No. 4,017,550 teaches that cyclic acetals of acrolein can be hydroformylated in the presence of phosphine-modified cobalt carbonyl complexes of rhodium carbonyl complexes. The hydroformylation occurs predominantly on the terminal unsaturated carbon atom of the acrolein acetal.

Nothing in the prior art discloses how to selectively hydroformylate an acrolein acetal on an unsaturated carbon atom other than the terminal carbon atom. Internal hydroformylation of an acrolein acetal is desirable because the hydroformylated product can be readily hydrolyzed to 2-methyl-1,3-propanediol. In turn, the 2-methyl-1,3-propanediol can be dehydrated by methods known to the art to produce 2-methyl-1-propen-3-ol. The 2-methyl-1-propen-3-ol is of interest because it can be oxidized by standard techniques to produce methacrylic acid or its corresponding esters. It follows that selective internal hydroformylation of acrolein acetals would be desirable because it affords a convenient starting material for the preparation of methacrylic acid.

SUMMARY OF THE INVENTION

According to this invention, an acrolein acetal is selectively hydroformylated by contact at reactive conditions with a gaseous mixture of carbon monoxide and hydrogen in the presence of a catalytic amount of a rhodium-cobalt bimetallic cluster loaded on an amine resin. This one-step process unexpectedly effects hydroformylation predominantly on the unsaturated carbon atom adjacent to the carbon bearing two ether groups. The words "selective hydroformylation" are used to indicate that a greater percentage of the product is hydroformylated internally than is hydroformylated on the unsaturated terminal carbon.

DETAILED DESCRIPTION OF THE INVENTION

The acetals of acrolein to be hydroformylated by the instant process are well-known compounds and are readily obtainable. These acetals of acrolein have the following formula

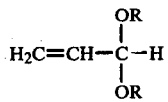

wherein each R is independently an aliphatic radical. In one preferred embodiment of this invention, both moieties represented by R in the foregoing formula are part of a single bivalent aliphatic radical. In this embodiment, the material to be hydroformylated is a cyclic acetal of acrolein.

The acetals of acrolein are readily manufactured by reacting acrolein with an alkanol or an alkanediol in the manner known to the art. These acetals are conveniently prepared by the treatment of acrolein with a large stoichiometric excess of a diol or alkanol at from 30° C.–50° C. in the presence of a strongly acid ion-exchange resin. The preferred starting materials are acrolein acetals of alkanediols having up to 6 carbon atoms or alkanols having from 1 to 4 carbon atoms. Particularly preferred acrolein acetals are those prepared by reacting acrolein with methanol, ethanol or ethylene glycol.

The supported catalysts used herein are prepared by loading onto an amine resin a bimetallic cluster of the formula:

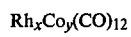

wherein x and y are individually integers from 1–3 with the proviso that the sum of (x+y) equals 4. These catalysts are further described and the method of their preparation detailed in U.S. Pat. No. 4,144,191, the relevant portions of which are incorporated herein by reference.

The acetals of acrolein are conveniently selectively hydroformylated in a liquid medium comprising a liquid solvent in which the bimetallic cluster and acrolein acetal are soluble and which is inert to both the reactants and products employed in the instant method. The acrolein acetal can be hydroformylated neat, i.e., in the absence of diluents, but generally it is preferred that a solvent be employed. Suitable solvents include hexane, benzene, xylene, o-dichlorobenzene, methylene chloride, carbon tetrachloride and chloroform, with toluene and tetrahydrofuran being preferred.

The temperature during hydroformylation is critical to the selective hydroformylation of the acrolein acetal in an internal position. The optimum temperature is dependent on the acetal, the solvent and other factors, but can be determined empirically by the skilled artisan without undue effort. Typically, a temperature in the range from about 50° C. to about 175° C., more preferably about 60° C. to about 150° C., most preferably about 75° C. to about 120° C., is conducive to internal hydroformylation of the acetal. Temperatures above these in the preferred ranges increase the hydroformylation of the unsaturated terminal carbon atom.

The pressure during hydroformylation is advantageously at least about 500 psia (pounds per square inch absolute), more preferably 750 to about 2000 psia. Pressures in the range from about 750 to about 1500 psia are especially preferred.

A gaseous mixture of hydrogen and carbon monoxide are reacted with the acrolein acetal to effect hydroformylation. Inert diluent gases, such as nitrogen can also be present in the mixture. The carbon monoxide and hydrogen are advantageously present in the gaseous mixture in a volume ratio in the range from 1:4 to 4:1, preferably from 1:2 to 2:1. Advantageously, a stoichiometric excess of carbon monoxide and hydrogen is employed with the acetal of acrolein.

The hydroformylation of the acrolein acetal produces the isomer hydroformylated on the terminal position as well as other products. These other products were not specifically identified, but appear to result from the isomerization of the double bond of the acrolein acetal. The desired hydroformylation product can be readily separated from the other products by fractional distillation or by other methods known to the art.

The following examples are illustrative of certain embodiments of the invention. All parts and percentages are by weight, unless indicated to the contrary.

EXAMPLE 1

Dowex® MWA-1 beads (0.25 g), an amine resin manufactured by The Dow Chemical Company which comprises a polystyrene backbone having a plurality of pendant benzyl dimethylamine functionality, and 0.2 g of a bimetallic cluster of the formula $Rh_2Co_2(CO)_{12}$ are mixed and agitated under an argon atmosphere for 12 hours at 20° C. The modified beads, i.e., the catalyst are then filtered and dried under vacuum.

The catalyst (0.2 g) is charged to a rocking autoclave along with 1 g of acrolein dimethyl acetal and 4 ml of toluene. The contents of the autoclave are sparged with nitrogen. The autoclave is pressurized to 1200 psia with an equimolar mixture of carbon monoxide and hydrogen and heated to 110° C. After 6 hours, the reactor is allowed to cool. The liquid present is analyzed by gas chromatography and proton magnetic resonance. These analyses indicate that 100 percent conversion occurs with a 50.4 mole percent yield of 2-(methylol)propanal dimethyl acetal and only 12.1 mole percent yield of 4-hydroxybutanal dimethyl acetal. The remaining portion of the hydroformylated product is a mixture of unidentified by-products.

EXAMPLES 2-4

In the manner described in Example 1, 1 g of acrolein diethyl acetal in 4 ml of solvent is hydroformylated in a rocking autoclave for 6 hours. In Examples 2 and 3, the solvent is toluene and the hydroformylation conditions are 75° C. in Example 2 and 115° C. in Example 3. In Example 4, the solvent is tetrahydrofuran and a temperature of 115° C. is maintained.

The liquid product from each example is analyzed by conventional techniques. The mole percentages of 2-(methylol)propanal diethyl acetal (Compound A) and 4-hydroxybutanal diethyl acetal (Compound B) are tabulated in Table I.

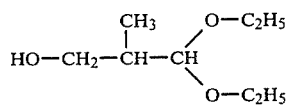

A

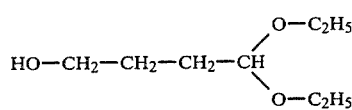

B

TABLE I

| Example | Conversion | Compound A | Compound B |
|---------|------------|------------|------------|
| 2 | 100% | 81 | 6.6 |

TABLE I-continued

| Example | Conversion | Compound A | Compound B |
|---------|------------|------------|------------|
| 3 | 100% | 69.5 | 6.4 |
| 4 | 100% | 85.4 | 3.6 |

EXAMPLES 5-7

In a manner described in Example 1, 1 g of the acrolein acetal of 1,2-butanediol in 4 ml of toluene is hydroformylated in a rocking autoclave. The hydroformylation temperature in Example 5 is 60° C., in Example 6 is 75° C. and in Example 7 is 115° C. In each instance, hydroformylation conditions are maintained for 6 hours.

The liquid product from each example is analyzed by conventional techniques. The mole percentages of the compounds in the product represented by the formulae C and D are tabulated in Table II.

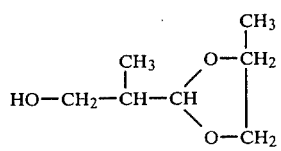

C

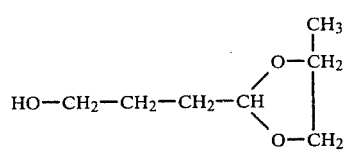

D

TABLE II

| Example | Conversion | Compound C | Compound D |
|---------|------------|------------|------------|
| 5 | 80% | 27.6 | 8.9 |
| 6 | 100% | 53.8 | 26.3 |
| 7 | 100% | 29.9 | 27.4 |

EXAMPLE 8

In the manner described in Example 1, 1 g of the acrolein acetal of 2-methyl-2,4-pentanediol in 4 ml of toluene is hydroformylated at 80° C. for 6 hours in a rocking autoclave. The liquid product is analyzed by conventional techniques. The mole percentages of the compounds in the product represented by formulae E and F are 45.9 percent and 26.5 percent, respectively.

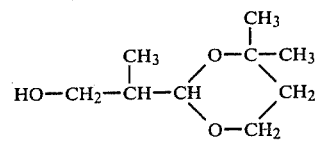

E

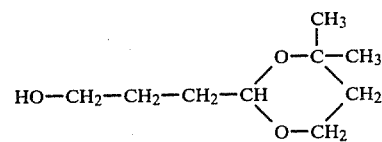

F

What is claimed is:

1. A one-step process for selectively hydroformylating an acetal of acrolein to a corresponding methylol acetal comprising contacting an acetal of acrolein with a gaseous mixture of carbon monoxide and hydrogen in the presence of a catalytic amount of a rhodium-cobalt bimetallic cluster loaded on an amine resin at a pressure of at least 500 p.s.i.a. and at a temperature in the range from about 50° to about 175° C., so as to effect hydroformylation predominantly on the acetal's unsaturated carbon atom adjacent to the carbon atom bearing two ether groups.

2. The process as described in claim 1 wherein the acrolein acetal is derived from methanol, ethanol or ethylene glycol.

3. The process as described in claim 1 wherein the acrolein acetal is derived from an alkanediol having up to 6 carbon atoms or an alkanol having from 1 to 4 carbon atoms.

4. The process as described in claim 3 wherein the hydroformylation is performed in a toluene or tetrahydrofuran solvent.

5. The process as described in claim 4 wherein the hydroformylation temperature is in the range from about 60° C. to about 150° C.

6. The process as described in claim 5 wherein the hydroformylation pressure is in the range from about 750 to about 2000 psia.

* * * * *

UNITED STATES PATENT AND TRADEMARK OFFICE
CERTIFICATE OF CORRECTION

PATENT NO. : 4,374,999
DATED : February 22, 1983
INVENTOR(S) : Philip E. Garrou

It is certified that error appears in the above—identified patent and that said Letters Patent is hereby corrected as shown below:

Column 1, line 27, "carbonyl complexes of rho-" should read -- carbonyl complexes or rho- --.

Signed and Sealed this

Twenty-third Day of August 1983

[SEAL]

Attest:

GERALD J. MOSSINGHOFF

Attesting Officer

Commissioner of Patents and Trademarks